(12) United States Patent
Govari et al.

(10) Patent No.: US 11,806,465 B2
(45) Date of Patent: Nov. 7, 2023

(54) ACCURATE IRRIGATION RATE MEASUREMENT SYSTEM AND METHOD

(71) Applicant: JOHNSON & JOHNSON SURGICAL VISION, INC., Irvine, CA (US)

(72) Inventors: Assaf Govari, Haifa (IL); Eran Aharon, Haifa (IL)

(73) Assignee: JOHNSON & JOHNSON SURGICAL VISION, INC., Irvine, CA (US)

( * ) Notice: Subject to any disclaimer, the term of this patent is extended or adjusted under 35 U.S.C. 154(b) by 118 days.

(21) Appl. No.: 17/357,587

(22) Filed: Jun. 24, 2021

(65) Prior Publication Data

US 2022/0409800 A1 Dec. 29, 2022

(51) Int. Cl.
*A61M 1/00* (2006.01)
*A61F 9/007* (2006.01)

(52) U.S. Cl.
CPC ............ *A61M 1/77* (2021.05); *A61F 9/00736* (2013.01); *A61M 1/74* (2021.05); *A61M 1/80* (2021.05); *A61M 2205/332* (2013.01); *A61M 2205/502* (2013.01); *A61M 2205/581* (2013.01); *A61M 2205/583* (2013.01); *A61M 2210/0612* (2013.01)

(58) Field of Classification Search
CPC ............ A61M 1/77; A61M 1/74; A61M 1/80; A61M 1/0058; A61M 1/0023; A61M 2205/60; A61M 2205/3393; A61F 9/007; A61F 9/00736; F04B 49/00; F04B 49/20; F04B 2205/05; F04B 2205/09
See application file for complete search history.

(56) References Cited

U.S. PATENT DOCUMENTS 4,134,297 A  1/1979 Herzl
6,690,280 B2  2/2004 Citrenbaum et al.
(Continued)

FOREIGN PATENT DOCUMENTS

WO  9716220 A1  5/1997
WO  2011064240 A1  6/2011
(Continued)

OTHER PUBLICATIONS

Lock-In Amplifier. Physics Open Lab, Aug. 20, 2019 [online], [retrieved on Dec. 6, 2022]. Retrieved from the Internet <URL: https://physicsopenlab.org/2019/08/20/lock-in-amplifier/>(Year: 2019).*

*Primary Examiner* — Erich G Herbermann
*Assistant Examiner* — Linnae E. Raymond
(74) *Attorney, Agent, or Firm* — Johnson & Johnson Surgical Vision, Inc.

(57) ABSTRACT

In one embodiment, an irrigated medical system includes a medical tool, an irrigation line configured to fluidically connect an irrigation reservoir storing irrigation fluid to the medical tool, and provide at least some of the irrigation fluid to the medical tool, a force sensor configured to be coupled with the irrigation reservoir, and provide a signal responsively to a force exerted by the irrigation reservoir on the force sensor over time as irrigation fluid in the irrigation reservoir is depleted, and a controller configured to find an irrigation rate of the irrigation fluid flowing in the irrigation line responsively to the signal.

16 Claims, 3 Drawing Sheets

(56) References Cited

U.S. PATENT DOCUMENTS

| | | |
|---|---|---|
| 10,463,780 B2 | 11/2019 | Mallough et al. |
| 2007/0172360 A1* | 7/2007 | Teipen ................ F04D 15/0209 |
| | | 417/36 |
| 2013/0060211 A1* | 3/2013 | Adams, Jr. ............ A61M 3/022 |
| | | 604/327 |
| 2016/0051746 A1* | 2/2016 | Case ................... A61M 1/3455 |
| | | 210/85 |
| 2017/0258976 A1* | 9/2017 | Hersenius ................ G08B 5/22 |
| 2019/0015589 A1* | 1/2019 | Shtram ............. A61M 5/16895 |
| 2021/0128815 A1 | 5/2021 | Byrne et al. |

FOREIGN PATENT DOCUMENTS

| | | | | |
|---|---|---|---|---|
| WO | WO-2016032457 A1 * | 3/2016 | ............... | E03B 7/00 |
| WO | WO-2016150754 A1 * | 9/2016 | ............... | E03B 7/00 |

\* cited by examiner

ACCURATE IRRIGATION RATE MEASUREMENT SYSTEM AND METHOD

FIELD OF THE INVENTION

The present invention relates to medical systems, and in particular, but not exclusively to, irrigation systems.

BACKGROUND

A cataract is a clouding and hardening of the eye's natural lens, a structure which is positioned behind the cornea, iris and pupil. The lens is mostly made up of water and protein and as people age these proteins change and may begin to clump together obscuring portions of the lens. To correct this a physician may recommend phacoemulsification cataract surgery. Before the procedure, the surgeon numbs the area with anesthesia. Then a small incision is made in the sclera or clear cornea of the eye. Fluids are injected into this incision to support the surrounding structures. The anterior surface of the lens capsule is then removed to gain access to the cataract. The surgeon then uses a phacoemulsification probe, which has an ultrasonic handpiece with a titanium or steel needle. The tip of the needle vibrates at ultrasonic frequency to sculpt and emulsify the cataract while a pump aspirates lens particles and fluid from the eye through the tip. The pump is typically controlled with a microprocessor.

The pump may be a peristaltic and/or a venturi type of pump for example. Aspirated fluids are replaced with irrigation of a balanced salt solution to maintain the anterior chamber of the eye. After removing the cataract with phacoemulsification, the softer outer lens cortex is removed with suction. An intraocular lens (IOL) is introduced into the empty lens capsule. Small struts called haptics hold the IOL in place. Once correctly implanted the IOL restores the patient's vision.

SUMMARY

There is provided in accordance with an embodiment of the present disclosure, a medical irrigation system, including a medical tool, an irrigation line configured to fluidically connect an irrigation reservoir storing irrigation fluid to the medical tool, and provide at least some of the irrigation fluid to the medical tool, a force sensor configured to be coupled with the irrigation reservoir, and provide a signal responsively to a force exerted by the irrigation reservoir on the force sensor over time as irrigation fluid in the irrigation reservoir is depleted, and a controller configured to find an irrigation rate of the irrigation fluid flowing in the irrigation line responsively to the signal provided by the force sensor.

Further in accordance with an embodiment of the present disclosure, the system includes a reservoir support coupled with the force sensor, and configured to support to the irrigation reservoir.

Still further in accordance with an embodiment of the present disclosure, the system includes a data interface, wherein the controller is configured to authenticate use of the irrigation reservoir responsively to receiving data from an integrated circuit of the irrigation reservoir via the interface.

Additionally, in accordance with an embodiment of the present disclosure the controller is configured to find the irrigation rate responsively to authenticating use of the irrigation reservoir.

Moreover, in accordance with an embodiment of the present disclosure, the system includes a pump disposed in the irrigation line, and configured to pump the irrigation fluid from the irrigation reservoir to the medical tool.

Further in accordance with an embodiment of the present disclosure the controller is configured to adjust a speed of the pump responsively to the found irrigation rate.

Still further in accordance with an embodiment of the present disclosure the controller is configured to modulate the speed of the pump responsively to a given frequency, and find the irrigation rate responsively to analyzing the signal at the given frequency.

Additionally, in accordance with an embodiment of the present disclosure the controller is configured to find the irrigation rate responsively to respective amplitudes of respective frequency transforms of respective sections of the signal at the given frequency.

Moreover, in accordance with an embodiment of the present disclosure the controller includes a lock-in amplifier configured to analyze the signal at the given frequency.

In addition, in accordance with another embodiment of the present disclosure the controller is configured to provide a notification to a user upon depletion of the reservoir determined by the irrigation rate. The notification may be an audible cue and/or a visual cue.

There is also provided in accordance with another embodiment of the present disclosure, a medical method of measuring an irrigation rate, including providing irrigation fluid from an irrigation reservoir to a medical tool via an irrigation line, providing a signal responsively to a force exerted by the irrigation reservoir on a force sensor over time as irrigation fluid in the irrigation reservoir is depleted, and finding an irrigation rate of the irrigation fluid flowing in the irrigation line responsively to the signal.

Further in accordance with an embodiment of the present disclosure, the method includes supporting the irrigation reservoir with a reservoir support coupled with the force sensor.

Still further in accordance with an embodiment of the present disclosure, the method includes authenticating use of the irrigation reservoir responsively to receiving data from an integrated circuit of the irrigation reservoir via an interface.

Additionally, in accordance with an embodiment of the present disclosure, the method includes finding the irrigation rate responsively to authenticating use of the irrigation reservoir.

Moreover, in accordance with an embodiment of the present disclosure, the method includes pumping the irrigation fluid from the irrigation reservoir to the medical tool via the irrigation line.

Further in accordance with an embodiment of the present disclosure, the method includes adjusting a speed of a pump responsively to the found irrigation rate.

Still further in accordance with an embodiment of the present disclosure, the method includes modulating the speed of the pump responsively to a given frequency, wherein the finding includes finding the irrigation rate responsively to analyzing the signal at the given frequency.

Additionally, in accordance with an embodiment of the present disclosure the finding includes finding the irrigation rate responsively to respective amplitudes of respective frequency transforms of respective sections of the signal at the given frequency.

Moreover, in accordance with an embodiment of the present disclosure, the method includes analyzing the signal at the given frequency using a lock-in amplifier.

In addition, in accordance with an embodiment of the present disclosure, the method includes further providing a notification to a user upon depletion of the reservoir based on the irrigation rate. The notification may be an audible cue and/or a visual cue.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
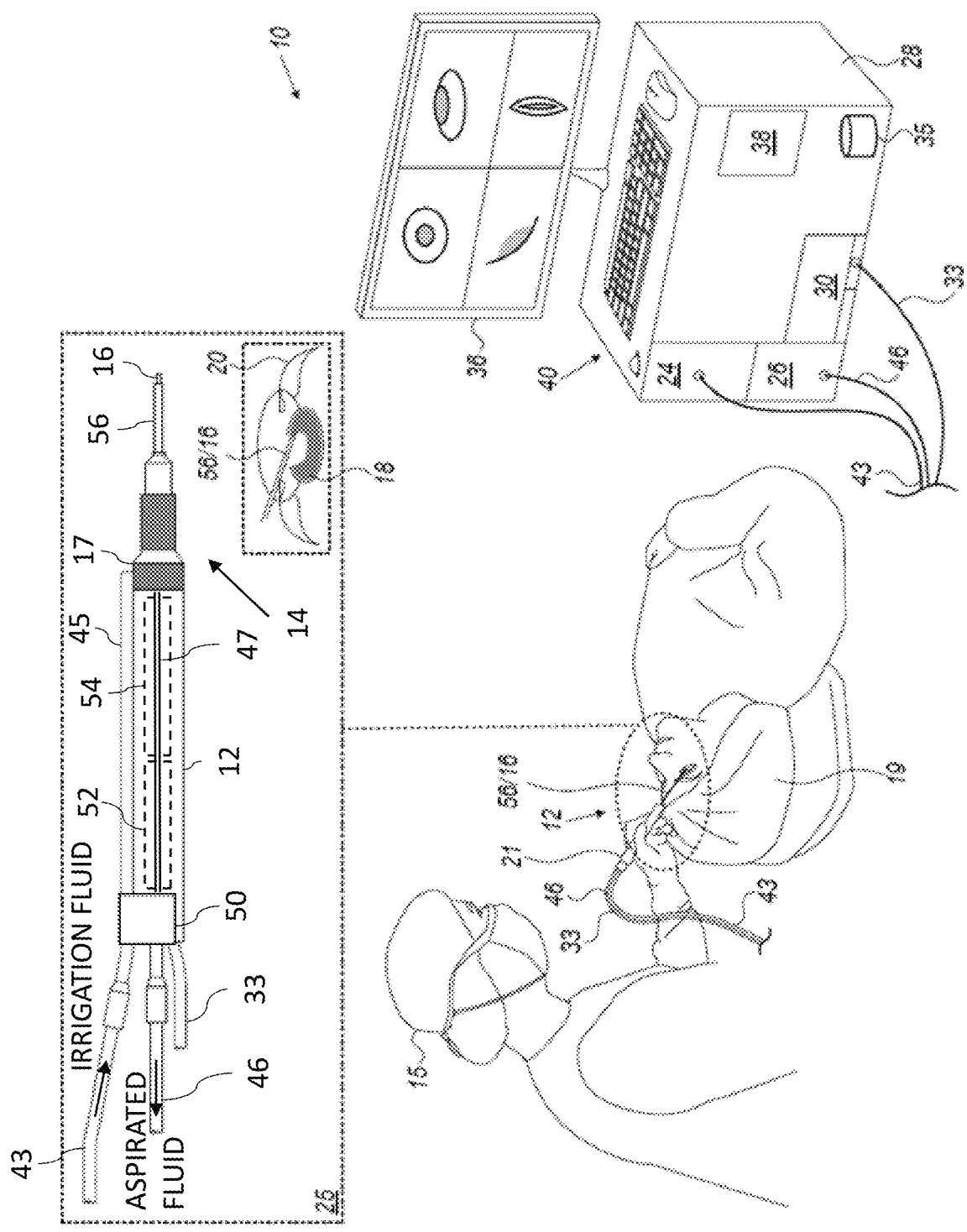
FIG. 1 is a partly pictorial, partly block diagram view of a phacoemulsification system constructed and operative in accordance with an embodiment of the present invention.

When operating on the eye, such as performing cataract surgery, the flow of fluid into and out of the eye are critical. While performing emulsification of the cataract, aspiration is needed to both bring the cataract into contact with the needle of the phacoemulsification probe so that the needle may sculpt and emulsify the cataract and also to remove particles of the cataract from the eye. As fluid and waste matter is removed from the eye an equal amount of fluid needs to be injected into the eye to ensure that adequate fluid is in the eye at all times. Additionally, it is essential that the pressure in the eye does not exceed safe limits. Also, it is generally desired by the physician performing the cataract surgery that the fluid pressure in the eye is as stable as possible.

Therefore, during cataract surgery it is important to control the irrigation and aspiration very carefully. For example, it is important to irrigate the eye at a stable irrigation rate over a period of time. Some pumps, for example, blower pumps, may not provide a stable irrigation rate.

At present, during cataract surgery the pressure of the irrigation fluid may be measured, but there is no direct measurement of the irrigation rate. Furthermore, any rate measurement must be able to accurately measure small rates of flow, of the order of fractions of ml/minute.

Embodiments of the present invention solve the above problems by measuring the mass of irrigation fluid left in the irrigation reservoir or bag over time for example using a force sensor such as a load cell. The irrigation rate is then found as a function of the change in mass of the irrigation reservoir measured by the force sensor over time and may be found based on a signal provided by the force sensor. Force sensors such as load cells are able to measure changes of micrograms, so that rates of fluid delivery may be measured accurately. The irrigation reservoir may be placed in, or suspended from, a support above the force sensor, which measures a compression force. In some embodiments, the irrigation reservoir may be suspended from a support below the force sensor, which measures a tensile force.

The found irrigation rate may be used to control a pump and/or valve in the irrigation line running between the irrigation reservoir and the probe. If the found irrigation rate is less than a first threshold, the speed of the pump is increased and/or the valve is opened more, and if the found irrigation rate is more than a second threshold, the speed of the pump is decreased and/or the valve is closed more.

In some implementations, the finding of the irrigation rate described above may be affected by noise in the system caused by movement of the irrigation reservoir and/or the irrigation line, for example, by the physician, which may incorporate noise into the signal provided by the force sensor. In some embodiments, the change in mass of the irrigation reservoir may be found more accurately in a noisy environment by modulating the pump speed at a given frequency. For example, if the speed is set at x, then the speed may be modulated from x minus y % to x plus y % according to a wave (e.g., sine wave) with a given frequency. The force measured by the force sensor may then be found by locking on to, or otherwise analyzing, the signal at the given frequency, for example, using a lock-in amplifier or an algorithm such as Goertzel algorithm, to determine the change in mass without noise or with reduced noise as described in disclosed embodiments.

System Description

Reference is now made to FIG. 1 is a partly pictorial, partly block diagram view of a phacoemulsification system 10 constructed and operative in accordance with an embodiment of the present invention.

The phacoemulsification system 10 comprises a phacoemulsification probe 12 (e.g., handpiece). In some embodiments, the phacoemulsification probe 12 may be replaced by any suitable medical tool for use in any suitable medical system. As seen in the pictorial view of phacoemulsification system 10, and in inset 25, phacoemulsification probe 12 comprises a probe body 17, and a distal end 14 including a needle 16 and a coaxial irrigation sleeve 56 that at least partially surrounds needle 16 and creates a fluid pathway between the external wall of the needle and the internal wall of the irrigation sleeve. The needle 16 is generally hollow to provide an aspiration channel. Moreover, irrigation sleeve 56 may have one or more side ports at, or near, the distal end to allow irrigation fluid to flow towards the distal end 14 of the phacoemulsification probe 12 through the fluid pathway and out of the port(s).

Needle 16 is configured for insertion into a lens capsule 18 of an eye 20 of a patient 19 by a physician 15 to remove a cataract. While the needle 16 (and irrigation sleeve 56) are shown in inset 25 as a straight object, any suitable needle may be used with phacoemulsification probe 12, for example, a curved or bent tip needle commercially available from Johnson & Johnson Surgical Vision, Inc., Santa Ana, Calif., USA.

In the embodiment of FIG. 1, during the phacoemulsification procedure, a pumping sub-system 24 comprised in a console 28 pumps irrigation fluid from an irrigation reservoir 60 (FIG. 2) to the irrigation sleeve 56 to irrigate the eye 20. The irrigation fluid is pumped via an irrigation tubing line 43 running from the console 28 to an irrigation channel 45 of probe 12. The distal end of the irrigation channel 45 includes the fluid pathway in the irrigation sleeve 56.

Eye fluid and waste matter (e.g., emulsified parts of the cataract) are aspirated via an aspiration channel 47, which extends from the hollow of needle 16 through the phacoemulsification probe 12, and then via an aspiration tubing line 46 to a collection receptacle in the console 28. The aspiration is affected by a pumping sub-system 26, also comprised in console 28.

System 10 may include a fluid dynamics cartridge 50, which may include one or more valves to regulate the flow of fluid in the irrigation channel 45 and/or aspiration channel 47 as well as sensors. Part of the irrigation channel 45 and the aspiration channel 47 is disposed in the probe body 17 and part is disposed in the removable cartridge 50.

Phacoemulsification probe 12 includes other elements, such as a piezoelectric crystal 52 coupled to a horn 54 to drive vibration of needle 16. The piezoelectric crystal 52 is configured to vibrate needle 16 (e.g., in a resonant vibration mode) to emulsify the lens capsule 18 of the eye 20. The vibration of needle 16 is used to break a cataract into small pieces during a phacoemulsification procedure. Console 28 comprises a piezoelectric drive module 30, coupled with the piezoelectric crystal 52, using electrical wiring running in a cable 33. Drive module 30 is controlled by a controller 38 and may convey processor-controlled driving signals via cable 33 to, for example, maintain needle 16 at maximal vibration amplitude. The drive module may be realized in hardware or software, for example, in a proportional-integral-derivative (PID) control architecture. The controller 38 may also be configured to receive signals from sensors in the phacoemulsification probe 12 and control one or more valves to regulate the flow of fluid in the irrigation channel 45 and/or the aspiration channel 47.

Controller 38 may receive user-based commands via a user interface 40, which may include setting a vibration mode and/or frequency of the piezoelectric crystal 52, and setting or adjusting an irrigation and/or aspiration rate of the pumping sub-systems 24/26. In some embodiments, user interface 40 and a display 36 may be combined as a single touch screen graphical user interface. In some embodiments, the physician 15 uses a foot pedal (not shown) as a means of control. Additionally, or alternatively, controller 38 may receive the user-based commands from controls located in a handle 21 of probe 12.

Some or all of the functions of controller 38 may be combined in a single physical component or, alternatively, implemented using multiple physical components. These physical components may comprise hard-wired or programmable devices, or a combination of the two, using digital and/or analogue processing. In some embodiments, at least some of the functions of controller 38 may be carried out by suitable software stored in a memory 35 (as shown in FIG. 1). This software may be downloaded to a device in electronic form, over a network, for example. Alternatively, or additionally, the software may be stored in tangible, non-transitory computer-readable storage media, such as optical, magnetic, or electronic memory.

The system shown in FIG. 1 may include further elements which are omitted for clarity of presentation. For example, physician 15 typically performs the procedure using a stereomicroscope or magnifying glasses, neither of which are shown. Physician 15 may use other surgical tools in addition to probe 12, which are also not shown in order to maintain clarity and simplicity of presentation.

Figure 2:
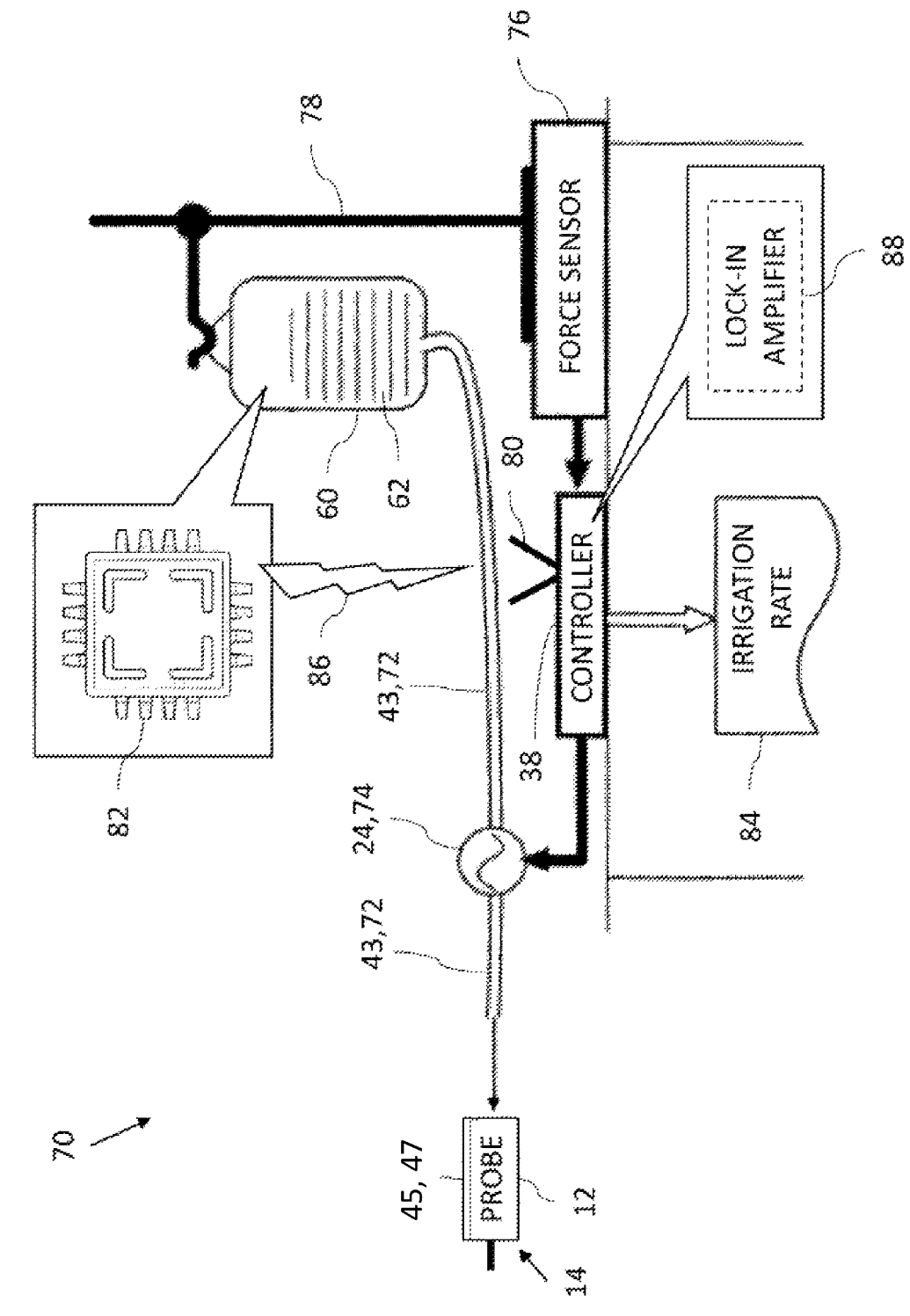
FIG. 2 is a partly pictorial, partly block diagram view of the irrigation sub-system of the phacoemulsification system of FIG. 1.
Figure 3:
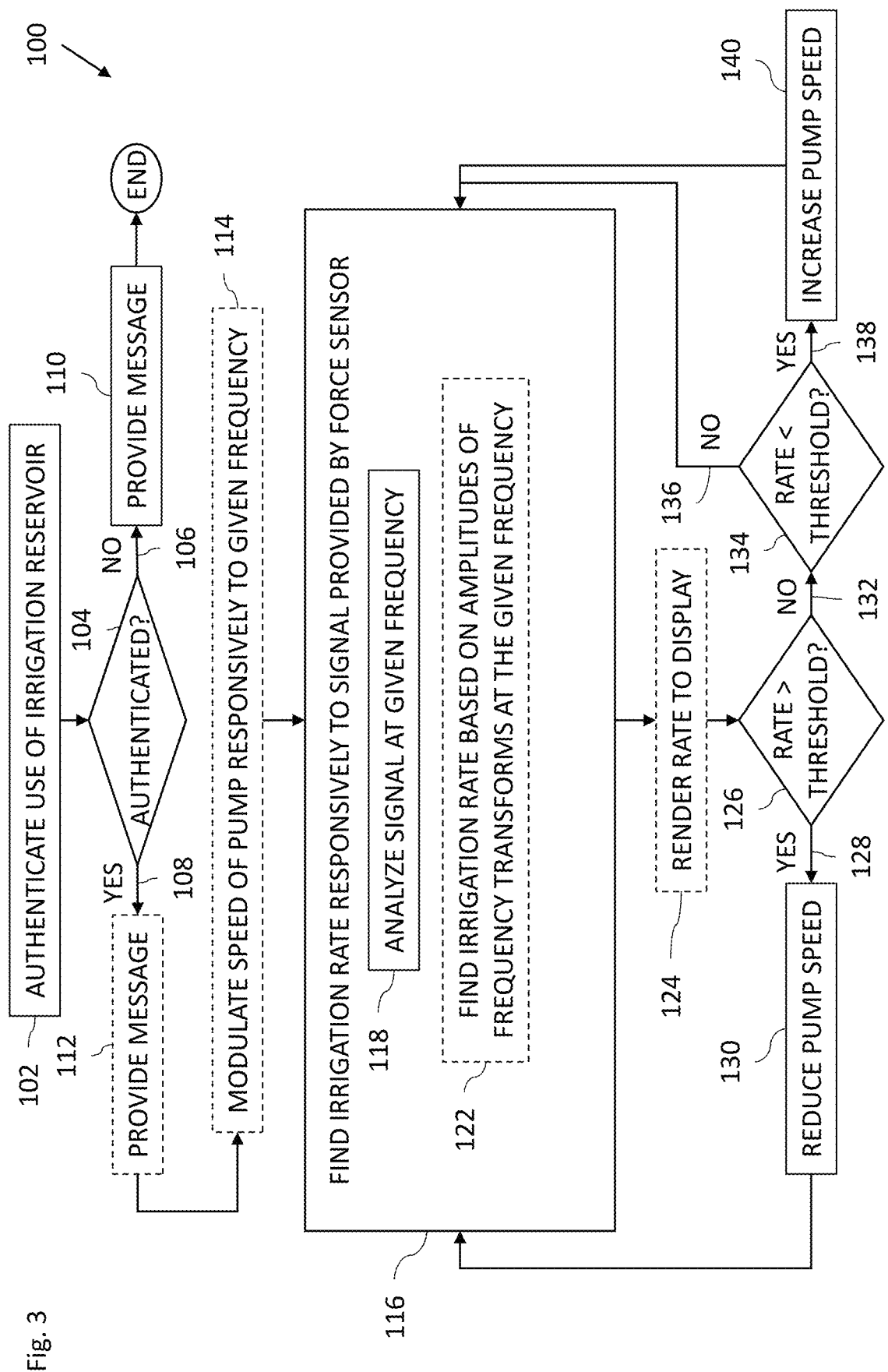
FIG. 3 is a flowchart including steps in a method of operation of the sub-system of FIG. 2.

Reference is now made to FIG. 2, which is a partly pictorial, partly block diagram view of an irrigation sub-system 70 of the phacoemulsification system 10 of FIG. 1. Reference is also made to FIG. 3, which is a flowchart 100 including steps in a method of operation of the sub-system 70 of FIG. 2.

The irrigation sub-system 70 includes the irrigation reservoir 60 (which may be a disposal irrigation bag or bottle) configured to store irrigation fluid 62. The irrigation sub-system 70 includes an irrigation line 72 (for example, including the irrigation tubing line 43 and the irrigation channel 45) extending from the irrigation reservoir 60 to the distal end 14 of phacoemulsification probe 12 or any suitable medical tool. Therefore, the irrigation line 72 is configured to fluidically connect the irrigation reservoir 60 storing the irrigation fluid 62 to the phacoemulsification probe 12 or any suitable medical tool. The irrigation line 72 is therefore configured to provide at least some of the irrigation fluid to the phacoemulsification probe 12 or any suitable medical tool.

The irrigation sub-system 70 may include the pumping sub-system 24, which includes a pump 74, disposed in the irrigation line 72, and configured to pump the irrigation fluid 62 from the irrigation reservoir 60 to the distal end 14 of the phacoemulsification probe 12 (or any suitable medical tool) via the irrigation line 72. The pump 74 may include any suitable pump, for example, a positive displacement pump, or a dynamic pump, such as a blower pump. In some embodiments, the irrigation fluid 62 is not pumped, but is gravity fed from the irrigation reservoir 60 to the distal end 14. In some embodiments, a valve (not shown) may be disposed in the irrigation line 72 to control the irrigation rate described in more detail below.

The irrigation sub-system 70 includes a force sensor 76 configured to be coupled with the irrigation reservoir 60, and provide a signal responsively to a force exerted by the irrigation reservoir 60 on the force sensor 76 over time as irrigation fluid 62 in the irrigation reservoir 60 is depleted due to irrigation fluid 62 being provided to the distal end 14 of the phacoemulsification probe 12 (or any suitable medical tool) via the irrigation line 72. The signal provided by the force sensor 76 is indicative of the change of mass of the irrigation fluid 62 in the irrigation reservoir 60 and may therefore be utilized in finding the irrigation rate of the irrigation fluid 62 flowing in the irrigation line 72 described in more detail below. The force sensor 76 may be any suitable device which provides an electrical signal as a function of force exerted on the device, e.g., a load cell.

The irrigation sub-system 70 includes a reservoir support 78 (e.g., stand) coupled with the force sensor 76, and configured to support to the irrigation reservoir 60 so as to enable the irrigation reservoir 60 to apply a gravitational force on the force sensor 76 in order for the force sensor to provide a signal indicative of the change of mass of the irrigation fluid 62 in the irrigation reservoir 60 over time. The irrigation reservoir 60 may be placed on or in the reservoir support 78 (e.g., in a pan or basket, or on a platform), or be suspended from the reservoir support 78 (e.g., by a hook or clip). The force sensor 76 may measure compression, e.g., when the support 78 is resting on the force sensor 76, or the force sensor 76 may measure tension, e.g., when the support 78 is suspended from the force sensor.

In some embodiments, the irrigation sub-system 70 includes a data interface 80, for example, a wired and/or wireless interface. The irrigation reservoir 60 (e.g., disposable irrigation bag) may include an integrated circuit 82 (e.g., a radio-frequency identification (RFID) tag connected to the outside of the irrigation bag) for identifying the irrigation reservoir 60 with the controller 38 to authenticate use of the irrigation reservoir 60. Authenticating the irrigation reservoir 60 may necessitate users of the phacoemulsification system 10 to buy only certain types of irrigation reservoirs (and accompanying irrigation fluid) to ensure quality and safety of the irrigation fluid 62 used with the system 10. In these embodiments, the controller 38 is configured to authenticate use of the irrigation reservoir 60 responsively to receiving data from the integrated circuit 82 of the irrigation reservoir 60 via the data interface 80 (block 102), for example, wirelessly (arrow 86) or via a wired connection or contacts. The authentication process may include receiving data stored in the integrated circuit 82 and confirming that the data identifies an approved irrigation reservoir. In some embodiments, the authentication process may include the controller 38 sending data to the integrated circuit 82 for processing and receiving data processed by the integrated circuit 82 in return and then checking if the data was processed correctly to confirm that the irrigation reservoir 60 is approved. In some embodiments, certain types of irrigation bags may be restricted by configuring the reservoir support 78 to only accept certain types of irrigation bags, for example, based on a size and/or shape of a pan, basket, platform, hook, and/or clip.

At a decision block 104, if the irrigation reservoir 60 is not authenticated (branch 106), the controller 38 is configured to render a message to the display 36 indicating that the irrigation reservoir 60 is non-approved (block 110). If the irrigation reservoir 60 is authenticated (branch 108), the controller 38 is optionally configured to render a message to the display 36 that the irrigation reservoir 60 is approved (block 112). One or more of the steps described below may be contingent upon the irrigation reservoir 60 being authenticated.

In some embodiments, due to noise generated in the irrigation sub-system 70, the controller 38 is configured to modulate the speed of the pump 74 responsively to a given frequency (block 114) as described in more detail below. For example, if the speed is set at x, then the speed may be modulated from x minus y % to x plus y % according to a wave (e.g., sine wave) with a given frequency. The value of y may be any suitable value, for example, in the range of 1 to 20. The value of y may be constant or variable or even random over time.

In some embodiments, the pump 74, e.g., a peristaltic pump may provide a modulated pumping rate as part of its normal operation. In these embodiments, the frequency of modulation of the pump 74 may be known based on the rotational speed and geometry of the pump 74.

The controller 38 is configured to find an irrigation rate 84 of the irrigation fluid 62 flowing in the irrigation line 72 responsively to the signal provided by the force sensor 76 (block 116). As previously mentioned, the signal provided by the force sensor 76 is indicative of the change of mass of the remaining irrigation fluid 62 in the irrigation reservoir 60 over time and may therefore be utilized in finding the irrigation rate of the irrigation fluid 62 flowing in the irrigation line 72 based on the known density of the irrigation fluid 62. In some embodiments, the controller 38 is configured to find the irrigation rate 84 responsively to authenticating use of the irrigation reservoir 60.

In some implementations, the finding of the irrigation rate 84 described above may be affected by noise in the irrigation sub-system 70 caused by movement of the irrigation reservoir 60 and/or the irrigation line 72, for example, by the physician, which may incorporate noise into the signal provided by the force sensor 76. In some embodiments, the change in mass of the irrigation reservoir 60 may be found more accurately in a noisy environment by modulating the pump speed at a given frequency. For example, if the speed is set at x, then the speed may be modulated from x minus y % to x plus y % according to a wave (e.g., sine wave) with a given frequency, as described above with reference to the step of block 114. The forces (e.g., masses) measured by the force sensor may then be found by locking on to, or otherwise analyzing, the signal at the given frequency, for example, using a lock-in amplifier 88 (comprised in the controller 38) or an algorithm such as Goertzel algorithm, to determine the mass (or change in mass) without noise or with reduced noise as described below in more detail.

Therefore, in some embodiments, the controller 38 is configured to: modulate the speed of the pump 74 responsively to a given frequency (block 114); and find the irrigation rate 84 responsively to analyzing the signal at the given frequency (block 118) as described in more detail below.

In some embodiments the lock-in amplifier 88, or a suitable analogue circuit, is configured to: receive a section of the signal from the force sensor 76 as input, analyze the section of the signal at the given frequency to find the amplitude of the signal without the noise, and provides an output which is indicative of the force exerted on the force sensor. The above may then be repeated for different sections of the signal to find the change in force or mass, which may then be used to find the irrigation rate 84 without noise or with reduced noise.

In some embodiments, the controller 38 is configured to use a Goertzel algorithm for the given frequency. The controller 38 is configured to: compute frequency transforms (e.g. from the time domain to the frequency domain, similar to Fourier transforms but just giving the transform values for the given frequency) responsively to respective sections of the signal at the given frequency (e.g., two frequency transforms for two sections of the signal); and find the irrigation rate 84 responsively to the respective amplitudes of the respective frequency transforms (block 122) using the Goertzel algorithm. The respective amplitudes of the respective frequency transforms at the given frequency are indicative of the force or mass of the irrigation reservoir 60 over time and may therefore be used to find the irrigation rate 84 without noise or with reduced noise.

The controller 38 is optionally configured to render the found irrigation rate 84 to the display 36 (block 124).

In some embodiments, the controller 38 is configured to adjust a speed of the pump 74 responsively to the found irrigation rate 84. For example, some pumps, e.g., blower pumps, do not provide a steady flow rate and therefore the speed may need to be adjusted to provide a steadier irrigation rate.

Therefore, at a decision block 126, the controller 38 checks if the found irrigation rate 84 is greater than a first threshold. If the found irrigation rate 84 is greater than the first threshold (branch 128), the controller 38 reduces the speed of the pump by a given increment (block 130) and processing continues with the step of block 116. If the found irrigation rate 84 is not greater than the first threshold (branch 132), processing continues at a decision block 134 at which the controller 38 checks if the found irrigation rate is less than a second threshold. If the found irrigation rate 84 is not less than the second threshold (branch 136), processing continues with the step of block 116. If the found irrigation rate 84 is less than the second threshold (branch 138), the controller 38 increases the speed of the pump by a given increment (block 140), and processing continues with the step of block 116. The values of the increments used to increase or reduce the speed of the 74 may be fixed or variable (e.g., proportion to the current speed), and may be the same for increases and decreases in speed, or different. The first threshold may be the same as the second threshold, or different. The first and second threshold may be set to default system values e.g., 20, 30, or 40 ml/minute, for example. In some embodiments, the first and second threshold are set or overridden by a user (e.g., the physician).

In some embodiments, the irrigation rate may be adjusted using a valve disposed in the irrigation line 72, such as an adjustable valve, which is opened more if the irrigation rate is less than the first threshold and closed more if the irrigation rate is greater than the second threshold.

In another embodiment, the controller 38 is configured to notify or warn a user via an audible cue or sound, e.g., an alarm, and/or a visual cue presented on the user interface 40 of when the irrigation reservoir 60 (e.g., bag or bottle) is close to being or is empty and thus requires replacement. The controller 38 is configured to determine the depletion of the fluid in the irrigation reservoir based on the irrigation rate. The type of notification and/or the timing of the notification may be automatically determined by the system or may be set by a user and be based on the amount of fluid that has been used or the amount of fluid that remains in the fluid reservoir as determined by the irrigation rate and/or thresholds described herein. In an embodiment, one or more notifications corresponding to one or more fluid thresholds or levels may be programmed or set to provide information to a user on the amount of fluid in the fluid reservoir during the procedure.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical irrigation system, comprising: a medical tool; an irrigation line configured to fluidically connect an irrigation reservoir storing irrigation fluid to the medical tool, and provide at least some of the irrigation fluid to the medical tool; a force sensor configured to be coupled with the irrigation reservoir, and provide a signal responsively to a force exerted by the irrigation reservoir on the force sensor over time as irrigation fluid in the irrigation reservoir is depleted; a controller configured to find an irrigation rate of the irrigation fluid flowing in the irrigation line responsively to the signal provided by the force sensor; and a pump disposed in the irrigation line, and configured to pump the irrigation fluid from the irrigation reservoir to the medical tool; wherein the controller is configured to: modulate the speed of the pump responsively to a given frequency; and find the irrigation rate responsively to analyzing the signal at the given frequency; and wherein the controller is configured to find the irrigation rate responsively to respective amplitudes of respective frequency transforms of respective sections of the signal at the given frequency.

2. The system according to claim 1, further comprising a reservoir support coupled with the force sensor, and configured to support the irrigation reservoir.

3. The system according to claim 2, further comprising a data interface, wherein the controller is configured to authenticate use of the irrigation reservoir responsively to receiving data from an integrated circuit of the irrigation reservoir via the interface.

4. The system according to claim 3, wherein the controller is configured to find the irrigation rate responsively to authenticating use of the irrigation reservoir.

5. The system according to claim 1, wherein the controller is configured to adjust the speed of the pump responsively to the found irrigation rate.

6. The system according to claim 1, wherein the controller comprises a lock-in amplifier configured to analyze the signal at the given frequency.

7. The system according to claim 1, wherein the controller is configured to provide a notification to a user upon depletion of the reservoir determined by the irrigation rate.

8. The system according to claim 7, wherein the notification is selected from the group consisting of an audible cue and a visual cue.

9. A medical method of measuring an irrigation rate, comprising: providing irrigation fluid from an irrigation reservoir to a medical tool via an irrigation line; providing a signal responsively to a force exerted by the irrigation reservoir on a force sensor over time as irrigation fluid in the irrigation reservoir is depleted; finding an irrigation rate of the irrigation fluid flowing in the irrigation line responsively to the signal; pumping the irrigation fluid from the irrigation reservoir to the medical tool with a pump via the irrigation line; and modulating the speed of the pump responsively to a given frequency, wherein the finding includes finding the irrigation rate responsively to analyzing the signal at the given frequency, and wherein the finding includes finding the irrigation rate responsively to respective amplitudes of respective frequency transforms of respective sections of the signal at the given frequency.

10. The method according to claim 9, further comprising supporting the irrigation reservoir with a reservoir support coupled with the force sensor.

11. The method according to claim 10, further comprising authenticating use of the irrigation reservoir responsively to receiving data from an integrated circuit of the irrigation reservoir via an interface.

12. The method according to claim 11, further comprising finding the irrigation rate responsively to authenticating use of the irrigation reservoir.

13. The method according to claim 9, further comprising adjusting the speed of the pump responsively to the found irrigation rate.

14. The method according to claim 9, further comprising analyzing the signal at the given frequency using a lock-in amplifier.

15. The method according to claim 9, further comprising providing a notification to a user upon depletion of the reservoir based on the irrigation rate.

16. The method according to claim 15, wherein the notification is selected from the group consisting of an audible cue and a visual cue.

* * * * *